(12) United States Patent
Ganesh

(10) Patent No.: US 10,231,664 B2
(45) Date of Patent: Mar. 19, 2019

(54) METHOD AND APPARATUS TO PREDICT, REPORT, AND PREVENT EPISODES OF EMOTIONAL AND PHYSICAL RESPONSES TO PHYSIOLOGICAL AND ENVIRONMENTAL CONDITIONS

(71) Applicant: Raghav Ganesh, San Jose, CA (US)

(72) Inventor: Raghav Ganesh, San Jose, CA (US)

( * ) Notice: Subject to any disclaimer, the term of this patent is extended or adjusted under 35 U.S.C. 154(b) by 374 days.

(21) Appl. No.: 15/166,162

(22) Filed: May 26, 2016

(65) Prior Publication Data

US 2017/0340270 A1 Nov. 30, 2017

(51) Int. Cl.
*A61B 5/00* (2006.01)
*A61B 5/16* (2006.01)
(Continued)

(52) U.S. Cl.
CPC .......... *A61B 5/4836* (2013.01); *A61B 5/0022* (2013.01); *A61B 5/0205* (2013.01);
(Continued)

(58) Field of Classification Search
CPC .................. A61M 21/00; A61M 21/02; A61M 2021/0005; A61M 2021/0022;
(Continued)

(56) References Cited

U.S. PATENT DOCUMENTS

| 6,853,304 | B2 | 2/2005 | Reisman |
| 8,630,633 | B1 * | 1/2014 | Tedesco .................... A61F 4/00 434/132 |

(Continued)

FOREIGN PATENT DOCUMENTS

| WO | WO2009154456 | 12/2009 |
| WO | WO2010120945 | 10/2010 |

(Continued)

*Primary Examiner* — Carrie R Dorna

(74) *Attorney, Agent, or Firm* — Inventive Law Inc.; Jim H. Salter

(57) ABSTRACT

A method and apparatus to detect environmental triggers of stress and antecedent physiological stress symptoms of a patient, followed up with delivery of stress relieving therapeutic response to the patient and a chronological report of events. An embodiment comprises a first device worn by the patient that contains sensors and can transmit and receive signals and a second device used by the caregiver that can transmit and receive signals. This integrated system continuously monitors environmental triggers and physiological stress indicative parameters of a patient diagnosed with autistic spectrum disorder, or other emotional or physical disorders, and compares these parameters against thresholds for the parameters. These thresholds can be configured automatically by the system—based on past episodes—or manually by the caregiver, or using automatically configured thresholds that are fine-tuned by the caregiver. When the parameters exceed the configured thresholds, several responses can be automatically generated by the system including: 1) generating therapeutic calming responses and cues to the patient to alleviate the episode, 2) sending notifications to the caregiver's device for intervention, and 3) creating a chronological assessment report of environmental stress triggers, antecedent physiological stress symptoms, and the resultant behavior of the patient.

10 Claims, 22 Drawing Sheets

(51) Int. Cl.
  *A61H 1/00*  (2006.01)
  *A61M 21/00*  (2006.01)
  *A61B 5/0205*  (2006.01)
  *G06F 19/00*  (2018.01)
  *G16H 40/67*  (2018.01)
  *A61H 23/02*  (2006.01)
  *A61H 39/00*  (2006.01)
  *A61B 5/11*  (2006.01)
  *A61B 7/00*  (2006.01)
  *A61B 5/08*  (2006.01)
  *A61B 5/1455*  (2006.01)

(52) U.S. Cl.
  CPC ............ *A61B 5/165* (2013.01); *A61B 5/4094* (2013.01); *A61B 5/6804* (2013.01); *A61B 5/746* (2013.01); *A61B 5/7465* (2013.01); *A61H 1/008* (2013.01); *A61H 23/02* (2013.01); *A61H 39/007* (2013.01); *A61M 21/00* (2013.01); *G06F 19/00* (2013.01); *G16H 40/67* (2018.01); *A61B 5/0816* (2013.01); *A61B 5/1118* (2013.01); *A61B 5/14551* (2013.01); *A61B 5/4266* (2013.01); *A61B 7/00* (2013.01); *A61B 2560/0242* (2013.01); *A61H 2201/10* (2013.01); *A61H 2201/102* (2013.01); *A61H 2201/165* (2013.01); *A61H 2201/5084* (2013.01); *A61H 2230/00* (2013.01); *A61H 2230/208* (2013.01); *A61H 2230/505* (2013.01); *A61H 2230/605* (2013.01); *A61H 2230/655* (2013.01); *A61M 2021/005* (2013.01); *A61M 2021/0016* (2013.01); *A61M 2021/0027* (2013.01); *A61M 2205/3306* (2013.01); *A61M 2205/3358* (2013.01); *A61M 2205/3368* (2013.01); *A61M 2205/3375* (2013.01); *A61M 2205/502* (2013.01); *A61M 2205/581* (2013.01); *A61M 2205/582* (2013.01); *A61M 2205/583* (2013.01); *A61M 2230/205* (2013.01); *A61M 2230/60* (2013.01); *A61M 2230/63* (2013.01); *A61M 2230/65* (2013.01)

(58) Field of Classification Search
  CPC .. A61M 2021/0027; A61M 2021/0044; A61M 2021/005; A61B 5/0022; A61B 5/4836; A61B 5/6803; A61B 5/6804; A61B 5/6805; A61B 5/6806
  See application file for complete search history.

(56) References Cited

U.S. PATENT DOCUMENTS

| | | | |
|---|---|---|---|
| 8,825,479 | B2 | 9/2014 | Krishnan |
| 2005/0187590 | A1 | 8/2005 | Boveja |
| 2008/0222769 | A1* | 9/2008 | Natonson ............ A61H 9/0078 2/70 |
| 2010/0331606 | A1* | 12/2010 | Wong .................... A61M 21/02 600/27 |
| 2012/0071781 | A1 | 3/2012 | Fadem |
| 2013/0078600 | A1 | 3/2013 | Fischer |
| 2013/0131483 | A1 | 5/2013 | Chen |
| 2013/0245396 | A1 | 9/2013 | Berman |
| 2014/0194788 | A1 | 7/2014 | Muehlbauer |
| 2014/0247343 | A1* | 9/2014 | Chen .................... G02B 27/017 348/135 |
| 2014/0334653 | A1* | 11/2014 | Luna ...................... G05B 15/02 381/332 |
| 2014/0379352 | A1 | 12/2014 | Gondi |

FOREIGN PATENT DOCUMENTS

| | | |
|---|---|---|
| WO | WO2012046068 | 4/2012 |
| WO | WO2014120084 | 8/2014 |

\* cited by examiner

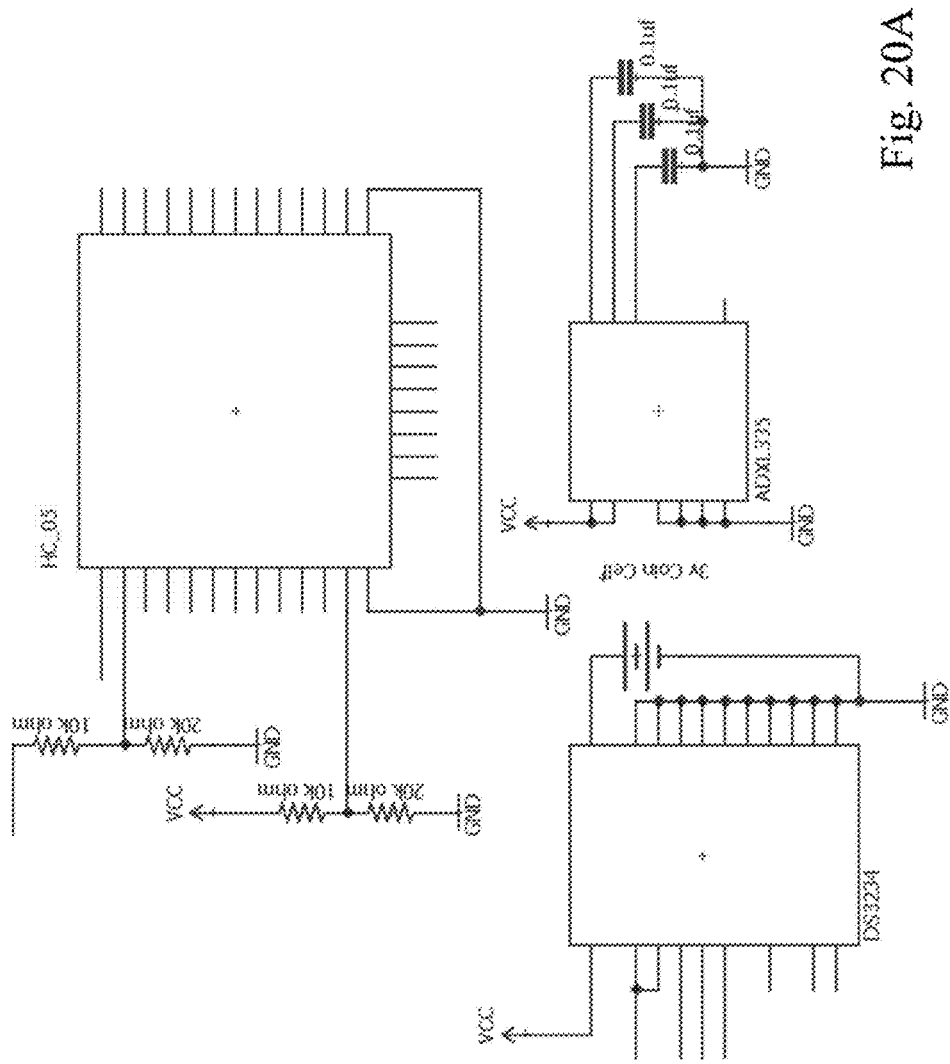

METHOD AND APPARATUS TO PREDICT, REPORT, AND PREVENT EPISODES OF EMOTIONAL AND PHYSICAL RESPONSES TO PHYSIOLOGICAL AND ENVIRONMENTAL CONDITIONS

TECHNICAL FIELD

This disclosure of various example embodiments relates generally to biomedical engineering and more particularly to assistive technology that aids the diagnosis and management of an individual's emotional and physical responses to physiological and environmental conditions.

BACKGROUND

According to the fifth edition of Diagnostic and Statistical Manual of Mental Disorders (DSM-5), published by American Psychiatric Association in May 2013, mental disorder is a syndrome characterized by clinically significant disturbance in an individual's cognition, emotion regulation, or behavior that reflects a dysfunction in the psychological, biological, or developmental process underlying mental functioning. Further, the definition of Autism Spectrum Disorder (ASD) can be summarized as the diagnosis given to a wide range of symptoms and severity of neurodevelopmental disorder that impairs an individual's ability to communicate and interact with others. It also includes restricted repetitive behaviors, interests and activities. There is usually significant distress or disability in social or occupational activities.

About 1 in 68 children aged 8 years have been identified with autism spectrum disorder (ASD) based on data collected in 2010 by CDC's Autism and Developmental Disabilities Monitoring (ADDM) Network and published in 2014.

There are no biological tests to diagnose conditions on the ASD. Clinicians and researchers diagnose and classify ASD, based on behavioral symptoms as defined in DSM-5. ASD is a life-long disorder; ASD children grow up into ASD adults. Autism is a heterogeneous disorder; the triggers and therapeutic response for coping are diverse and differ from person to person. About 40% of the children diagnosed with ASD are unable to communicate verbally. ASD boys have been found to be more easily irritable than boys with no psychopathology, and resembling boys with severe mood dysregulation. Several studies have noted higher episodes of elevated anxiety and emotional dysregulation being part of the symptomatology among individuals with ASD.

Also called by other labels such as "socially inappropriate behavior," "challenging behaviors," or "autistic 'meltdowns'," these are episodes of poorly modulated involuntary emotional outbursts in the ASD individuals that are often intense, frightening, frustrating, and risky. Autistic meltdowns are not goal-related temper tantrums and can be one of the most challenging parts of life for autistic person and his/her caregiver. These challenging behaviors add to the list of barriers to effective education, training, and social development of individuals diagnosed with ASD.

Autistic meltdowns are triggered from being extremely frustrated or stressed, sometimes for reasons that might appear insignificant and hence unexpected to the non-autistic. Causes of autistic meltdowns include, neurological and sensory overload, mounting frustrations over expectations to perform activities and behave within conventional norms, neurological difficulty adjusting to even minor deviations from routine, and failed attempts to be understood.

Autistic meltdowns may be prevented if the accumulating stress levels can be halted and reversed in the antecedent to meltdown phase, called the agitation phase or rumbling phase; referred henceforth herein as pre-meltdown phase. It is a challenge to detect the stress buildup leading to the meltdown phase. The time duration and the intensity of the pre-meltdown phase varies from one ASD person to another, and from one instance to another. Individuals diagnosed with ASD have atypical sensitivity to pain and other stimuli, which also varies from one ASD individual to another. For example, a study had 94% of the ASD individuals sample reporting extreme levels of sensory processing on at least one sensory quadrant of the ADULT/ADOLESCENT SENSORY PROFILE® from NCS PEARSON™, which is a questionnaire assessing levels of sensory processing in everyday life. Limited ability to convey signs or level of discomfort felt, and their early behavioral response to the stress inducing triggers often being subtle to distinguish from their normal behaviors are also challenges faced by the caregivers to timely interpret the early signs of accumulating stress among the ASD.

Upon detection of accumulating stress, mapping the instances of stress to the corresponding triggers would aid the caregiver and allow him or her to intervene and attenuate the triggers, thereby stopping the stress buildup. Further, a timely and specific therapeutic calming intervention, would aid in reducing an autistic person's stress level. The effectiveness of different intervention therapies may vary from person to person due to the high heterogeneity of the ASD individual's sensitivity to different stress triggers. Lateral pressure on the arms and/or torso has been found to comfort some ASD individuals. Music therapy has been documented as useful for calming some ASD individuals. For such individuals, specific comforting sounds could bring down their stress level. Hence, a configurable de-stressing solution to fit the unique needs of the ASD individual is needed.

Due to the above listed challenges, most of the existing methods to capture the causes for the autistic meltdown and dynamically provide timely interventions to prevent an autistic meltdown are often limited to health care or research in laboratories or medical facilities by trained specialists using a variety of distinct tools and methods. There is a need for in situ personalized care to predict and prevent episodes of autistic challenging behaviors.

Other types of disorders, such as epilepsy, can result in serious episodes of seizures or periods of unusual behavior, sensations, and sometimes loss of consciousness. There is a need for in situ personalized care to predict and prevent episodes of challenging behaviors for these conditions as well.

SUMMARY

The various example embodiments disclosed herein describe a device to predict, report, and prevent episodes of emotional and physical responses to physiological and environmental conditions. It is a technology-driven solution to improve in situ personalized care to people with autism, epilepsy, and other disorders that involve episodes of extreme emotional or physical responses. Personalized care and assistance is provided by responding to their emotional needs despite their limited verbal communication ability. This system and method allow monitoring of multiple environmental factors that can induce stress in the patient, and also can monitor multiple physiological symptoms. Monitoring the physiological symptoms would capture the impact of psychological sources of stress.

In real time, a sensor system, which includes a plurality of sensors for gathering and communicating sensor data, measures the accumulated stress values in a patient by reading two sets of sensors, one set of sensors that records environmental stimuli such as ambient sound and light, and a second set of sensors that records the patient's physiological conditions such as pulse rate and skin conductivity. The values of the sensors are repeatedly compared against pre-configured threshold values. When the sensor values exceed the pre-configured threshold values, the system determines that the patient has reached the pre-meltdown phase, also called antecedent to the meltdown phase.

When the system and method detect that the patient has entered the pre-meltdown phase, the system triggers a set of activities. These activities include providing multiple options to deliver a therapeutic calming response to the patient to prevent further escalation of the patient's stress levels. The type of therapeutic calming response can be controlled and pre-configured by the caregiver to match the needs of each individual patient. Examples of therapeutic responses include playing calming audible sounds to the patient, displaying calming images to the patient, activating dynamic compression vests worn by the patient, and activating compression massages to the patient.

The system and method also provide alert information to the mobile communication device of the caregiver. The alert information can include the sensor values that have exceeded the thresholds and past values of all or a subset of the sensors. Based on the system-generated alert, the caregiver may choose to intervene and personally de-escalate the stress in the patient. Examples of the caregiver intervention that would de-escalate the stress include moving the patient away from the stress inducing environment, and diverting the patient's attention to a relaxing activity. Based on an assessment of the chronological recorded values of the sensors, the caregiver can identify the correlation between the stress levels and environmental factors.

The system and method also provide alert information to the patient of the accumulating stress levels. The alert may be a combination of discreet haptic or audible information; the type of alert can be configured by the patient or caregiver. For example, the alert can be a cue for the patient to self-regulate in the pre-meltdown phase. The patient alert feature may also allow the caregiver to train the patient in detecting triggers that escalate their stress levels.

The system and method also chronologically store the sensor parameters and therapeutic response information. This information may be retrieved for analysis to tailor the thresholds of the sensor parameters, and for feedback to the patient or caregiver to improve the configuration of the system.

BRIEF DESCRIPTION OF THE DRAWINGS

FIGS. 20A through 20D and FIG. 21 show an example electronic circuit layout and electronic circuit schematic implementation of an example embodiment of the wearable device module that is worn by the patient).

DETAILED DESCRIPTION

Figure 1:
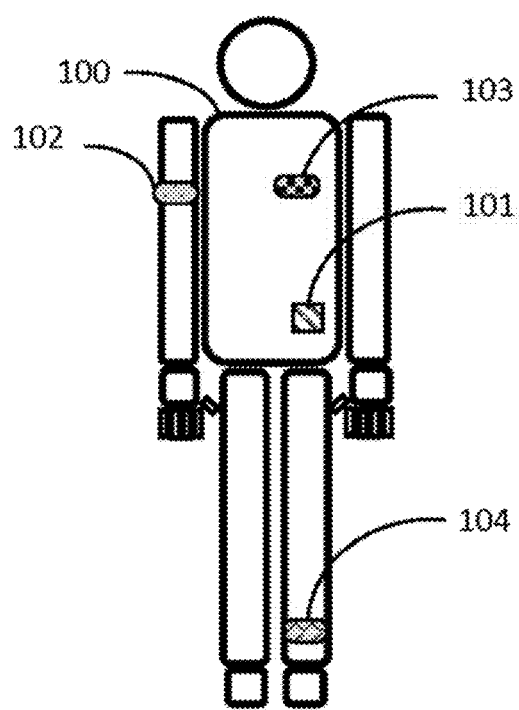
FIG. 1, FIG. 2, FIG. 3, and FIG. 4 show different example embodiments of the device being worn by a patient.
Figure 2:
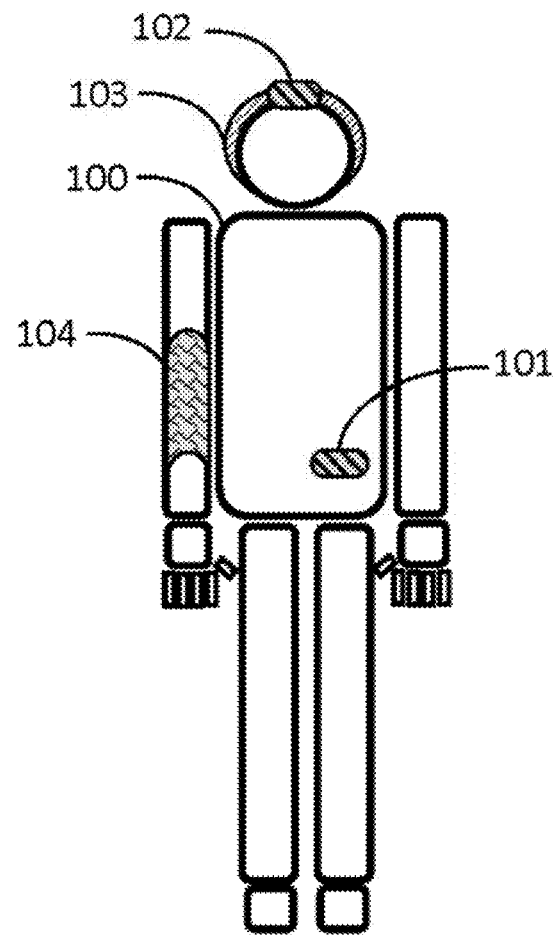
Figure 3:
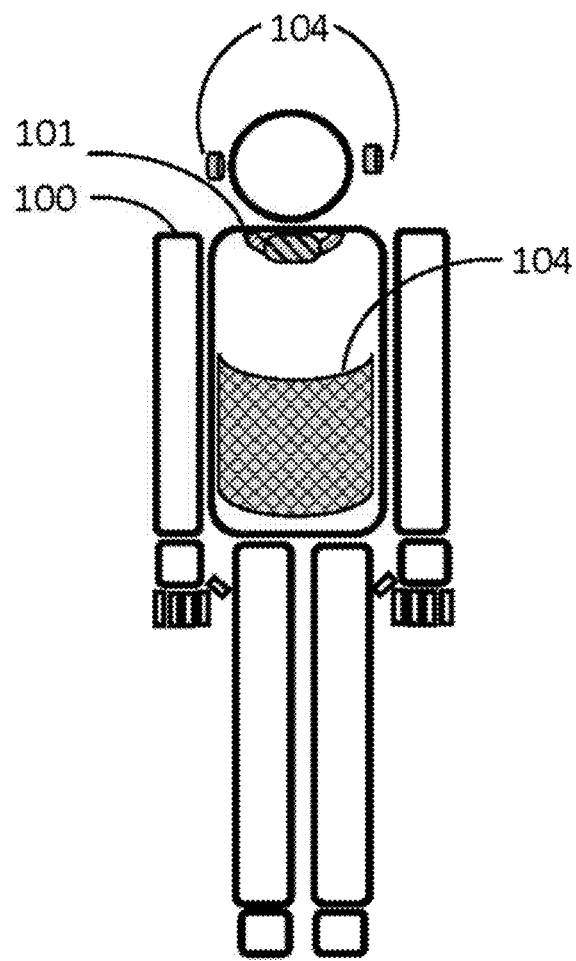
Figure 4:
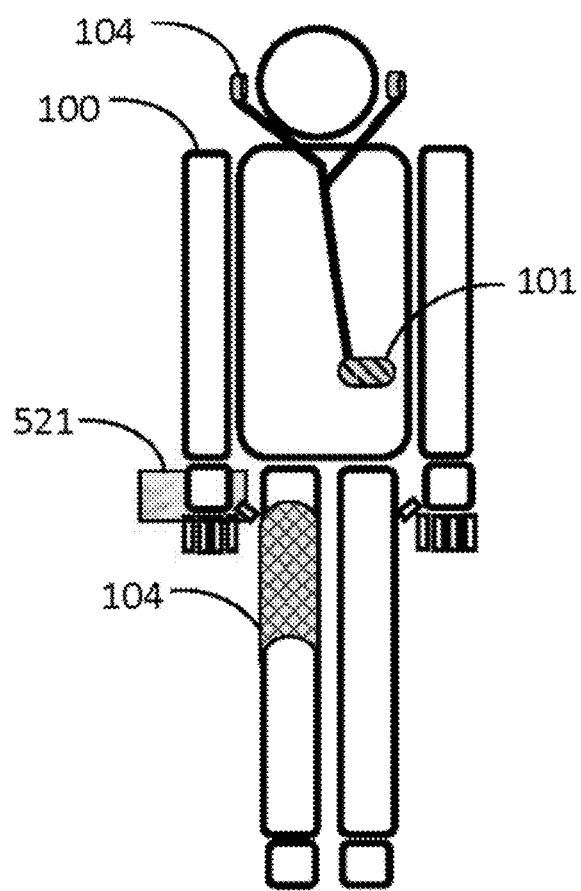

FIG. 1 through FIG. 4 show different example embodiments of the device being worn by patient 100. Environmental characteristics measuring sensor system 102, patient's physiological characteristics measuring sensor system 103, and therapy device 104 are distributed and fastened to the body of patient 100. In one embodiment shown in FIG. 1, the sensor systems and therapy devices are embedded in a garment worn (not shown) by the patient 100. FIG. 3 and FIG. 4 show example embodiments where two example therapy devices 104 such as music playing headphones and lateral pressure compression applying devices to the torso and limbs. The garment can have the sensor systems, and therapy devices either permanently sewed onto the garment or temporarily attached and detached from the garment. These devices communicate wirelessly or through wires, and interface through a controller 101. FIG. 3 shows an example embodiment where the controller 101 is worn as a collar to the garment. In this description the controller 101 is a microprocessor-based device. The controller 101 can be a mobile device, such as cell phone, or a dedicated stand-alone wearable electronic device with data processing capability. Another embodiment can have the controller distributed across multiple locations, which may also be integrated with the electronics of the sensors/transducers and therapy devices. The environmental sensor system 102, the physiological sensor system 103, and therapy device 104 can be distributed and worn at different parts of the body.

FIG. 4 shows one embodiment where the patient uses the caregiver's mobile device 521 as part of the system. This is an example where the patient is being trained to learn to self-regulate his/her emotional and physical response to physiological and environmental conditions.

Figure 5:
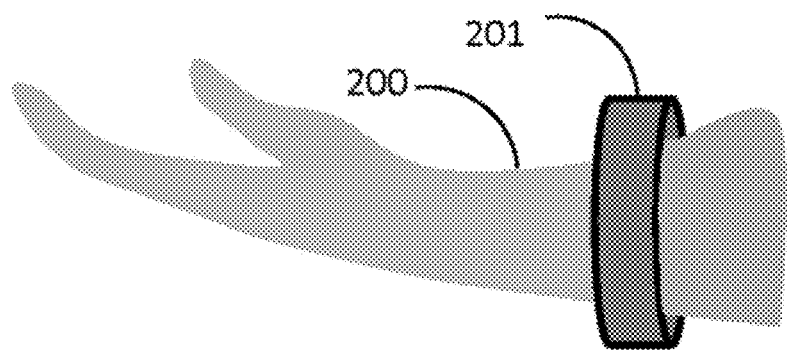
FIG. 5 and FIG. 6 show a close-up view of one embodiment of the device being worn on a patient's wrist.

FIG. 5 shows another example embodiment in the form of a bracelet 201 worn on the patient's wrist 200 or on the patient's ankle (not shown). Bracelet 201 comprises a controller 101 (not shown), environmental sensor system 102, physiological sensor system 103, and therapy device 104.

Figure 6:
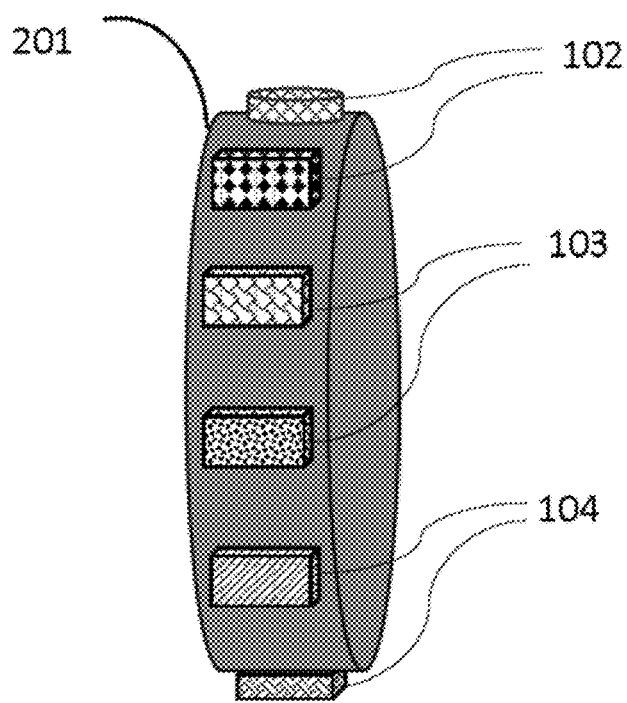

FIG. 6 shows a more detailed view of this embodiment in the form of a bracelet 201 comprising an environmental sensor system 102, physiological sensor system 103, a therapy device 104, and a controller 101 (not shown). A plurality of sensors (not shown) may include accelerometers, electro dermal skin conductivity sensors, gyroscopes, microphones, temperature sensors, humidity sensors, compasses, global positioning systems, and the like. Therapy devices (not shown) may include miniature ultrasonic therapy devices, micro motors to provide haptic feedback cues, miniature audible speakers, earphone connectors, wireless BLUETOOTH™ transmitters for earphones, controlling dynamic compression vests, and the like.

Figure 7:
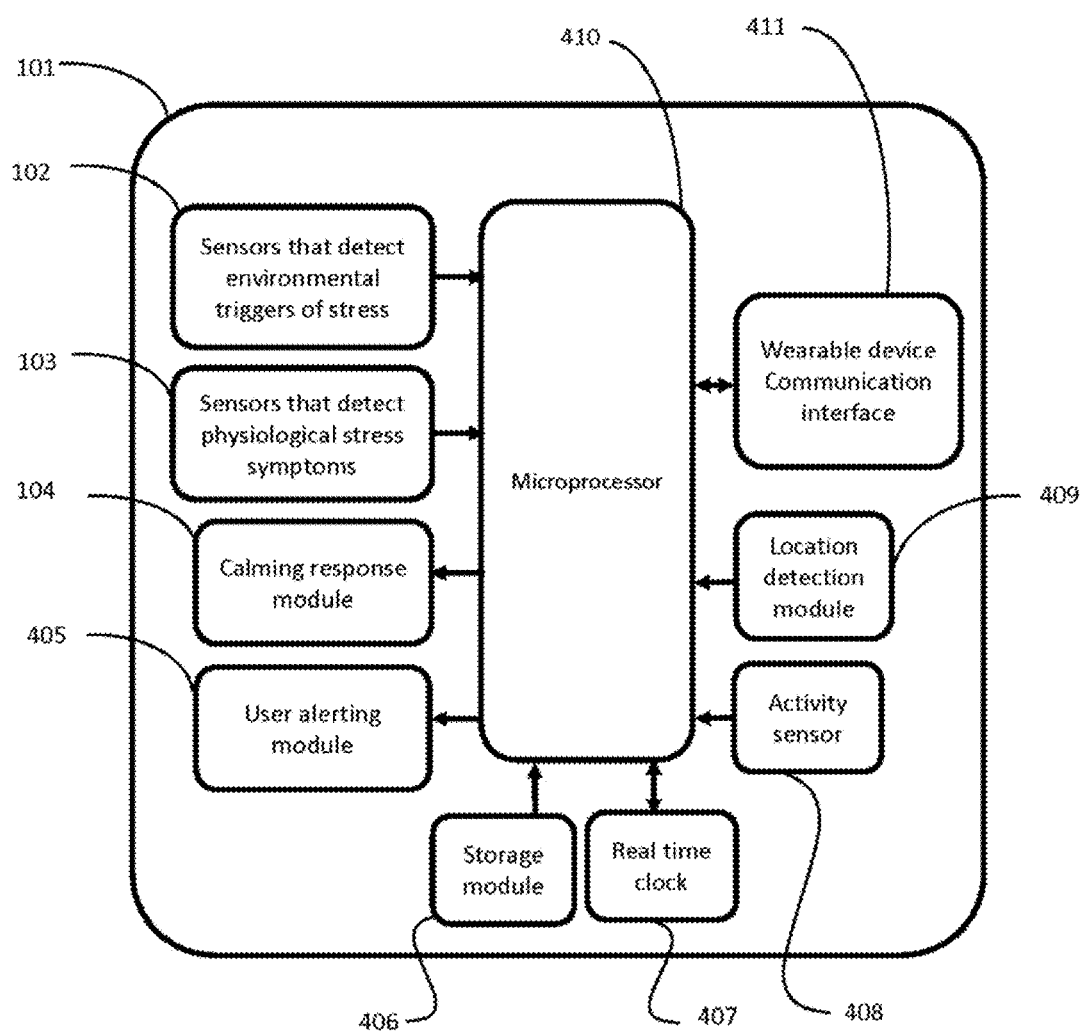
FIG. 7 is a block diagram illustrating the principal functionality of one embodiment of the part of the device that is wearable by the patient.

FIG. 7 is a block diagram illustrating a more detailed view of the principal functionality of one embodiment of the part of the system that is worn on the patient's wrist 200. The controller 101 includes a microprocessor/microcontroller 410 that may be interfaced with wearable device communication interface 411, storage module 406, and real time clock 407. The microprocessor 410 interfaces with environmental sensor system 102, physiological sensor system 103, and therapy device 104. The environmental sensor system 102 includes sensors that detect environmental triggers of stress, and sensors that detect activity of the patient 408. The physiological sensor system 103 includes transducers that detect physiological stress symptoms, and transducers that detect a physical activity level of the patient 408. The signals of pre-autistic meltdown may be gathered through at least two sets of sensor systems:

Category A: Sensors 102 that detect environmental sources of stress that may lead to meltdown, comprising light intensity, light wavelengths, sound level, sound frequency, sound pattern, air quality, humidity, temperature, barometric pressure, ambient electromagnetic radiation, ambient radiofrequency radiation, and Category B: Sensors 103 that detect physiological stress symptoms, comprising accelerometers that may detect restlessness, galvanic skin response sensors that may detect perspiration levels, flex resistors that may detect muscle tension, pulse oximetry sensors that detect various types of breathing patterns, including hypoventilation, when the patient is breathing room air, microphone that detects patient's audible frequency and vocal patterns.

The therapy device 104 consists of calming response devices, such as a compression vest and device to alert the patient 100 of the escalating stress levels. The patient can self-regulate their activity based on the cues from the patient alerting device 405. Sample patient alerting devices include devices such as LCD displays, LEDs, haptic, and audio feedback devices.

Figure 8:
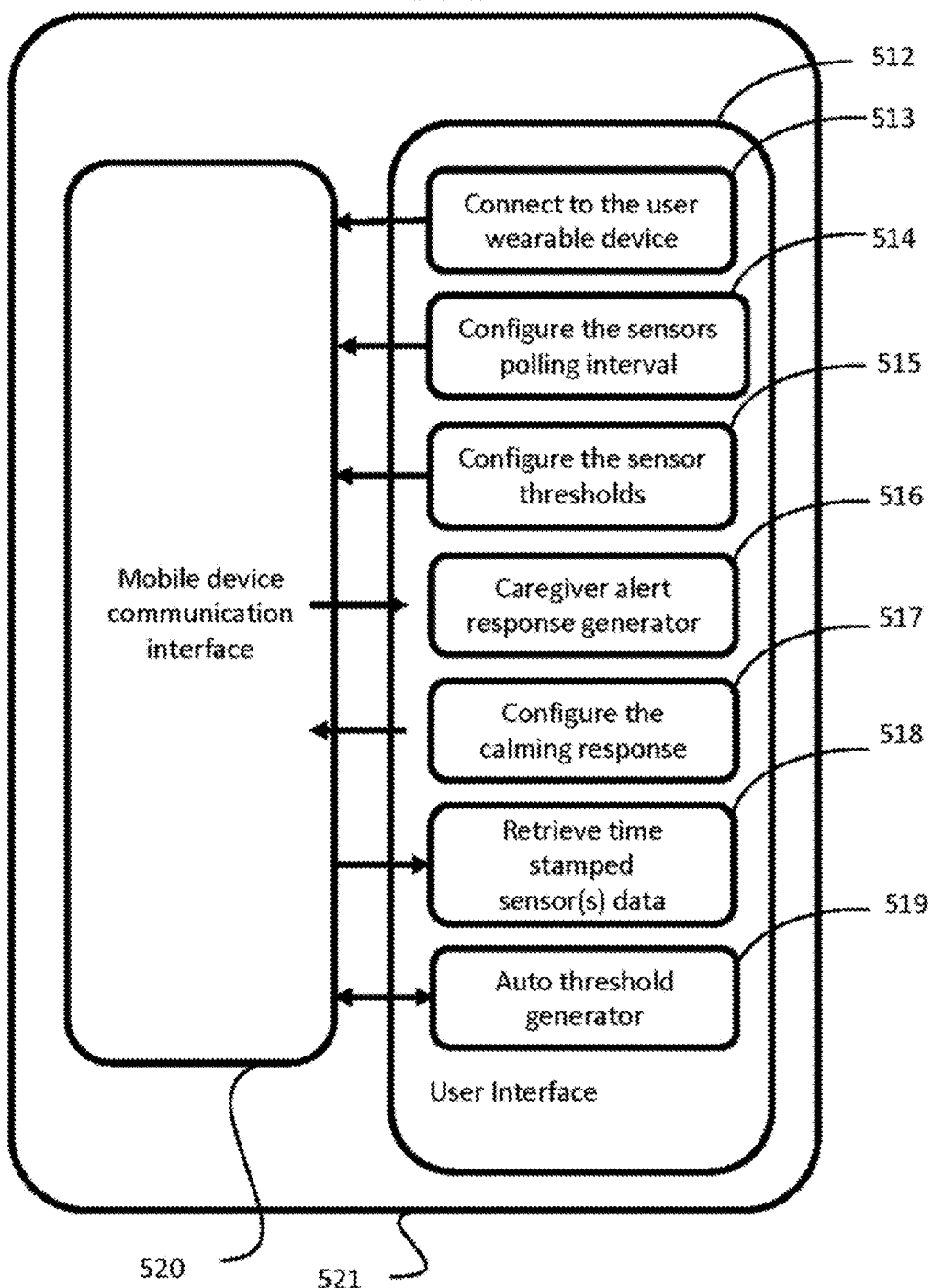
FIG. 8 is a block diagram illustrating the principal functionality of one embodiment of the part of the device that is used by the caregiver.

FIG. 8 is a block diagram illustrating the principal functionality of one embodiment of the part of the system that is used by the caregiver's mobile device 521. The wearable device communication interface may connect, wirelessly and/or with wires, to the caregiver's mobile device 521 through the mobile device communication interface 520. The wearable device communication interface 520 may in turn interface with user interface module 512, which in turn may consist of modules 513-519: a module to connect to the patient wearable device 513, a module to configure the sensors' polling intervals 514, a module to configure the sensor thresholds 515 to indicate normal range of the sensor values, a caregiver alert response generator 516 module, a module to configure the calming response 517, a module to retrieve time stamped sensor data 518, and a module to auto generate threshold 519.

Examples of the caregiver's mobile device 521 may include a tablet, Personal Digital Assistant (PDA), laptop, smart watch, smart glasses, smart band, or mobile phone, or a computing system that can communicate with the patient's wearable device using wired or wireless connection, such as through the internet. The components 101 (FIGS. 7) and 521 (FIG. 8) integrated together encompass the full functionality of an example embodiment. The wearable device communication interface 411 may use wired and/or wireless protocol to communicate with the mobile device. The aforementioned protocol may be a proprietary protocol or an industry standard protocol such as WI-FI®, RFID®, NFC®, BLUETOOTH®, USB®, THUNDERBOLT®, I2C®, ETHERNETTM™, and TCP/IP.

A combination of FIG. 7 and FIG. 8 together show an example embodiment of the functional integration of the user wearable environmental sensor system 102, physiological sensor system 103, controller 101, therapy device 104 and caregiver's mobile device 521. Periodically, the readings from the environmental sensor system 102 and the physiological sensor system 103, are monitored by the microprocessor 410 and compared with the sensors' corresponding threshold values 515. The caregiver's mobile device 521 and the patient wearable device 101 are connected, through the connection established between the electronics device communication interface 411 and the wearable device communication interface 520. Periodically, the readings from the environmental sensor system 102 and the physiological sensor system 103, are monitored by the microprocessor 410 and compared with the sensors' corresponding threshold values 515. The sensor threshold values are configured by either the caregiver and/or patient through the functionality configure the sensor thresholds module 515. The polling interval may be configured through the functionality to configure the sensors polling interval module 514. The threshold values indicate the normal non-meltdown range of the sensors specific to each individual patient. When the readings from the sensors cross the thresholds, the response initiated by microprocessor 410 comprises of the following:

Calming response to the patient is implemented through the calming response module 104, Alert information to the patient is initiated through the patient alerting module 405, Alert information to the caregiver is initiated through the caregiver alert response generator 516 module. The caregiver alert response is transmitted by the wearable device communication interface 411 to the caregivers' mobile communication device 521.

The actions that are dynamically controlled by the calming response module 104 include (example embodiments are shown in FIG. 2, FIG. 3, and FIG. 4) applying vibrations at select pressure points on the patients' body, applying deep pressure compression to specific locations of the lateral body surface, displaying a calming video or images, playing favorite music, playing a discrete gentle audible alert, and applying a haptic alert signal to the patient. Other calming devices and modes may be used that are consistent with the spirit of the various embodiments. The therapeutic calming response characteristics of the calming response module 104, such as duration and intensity of the responses, can be controlled by the 'configure the calming response module 517' that is located on the caregivers' mobile device 521.

The caregiver alert response generator 516 module supports a variety of modes to quickly alert the caregiver. These alerts are played on the caregiver mobile device 521 and could be one or more of the following: a haptic signal, an audible signal, an instant message, an email to caregivers' email accounts. Other alternate mediums may be used consistent with the spirit of the various embodiments. The list of devices that can be used as caregiver mobile device 521 comprises devices such as mobile phones, smart phones, smart watches, smart glasses, a smart band, an exercise band, a fitness band, tablets, laptop computers, notebook computers, and controllers of Internet of Things (IoT). The caregiver alert information comprises the current and past values of the sensor data, the details of the thresholds that were exceeded, the calming responses being provided to the patient, and the activity and location information of the patient. The activity sensor 408, such as an accelerometer, gyroscope, and compass may convey the patient's current activity level related information. The location sensor 409, such as a Global Positioning System (GPS), may convey the current location and/or orientation/motion information of the patient.

Figure 9:
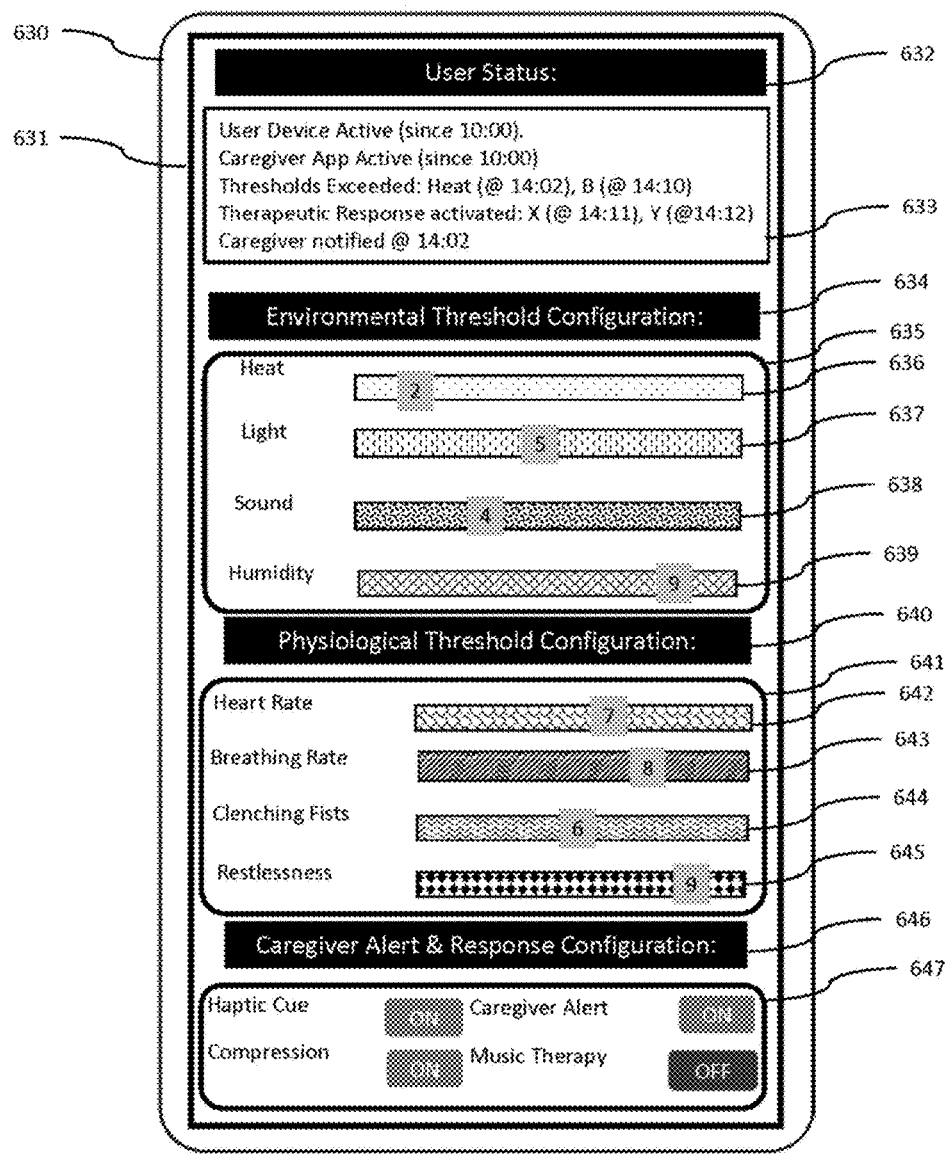
FIG. 9 is a screenshot of the graphical user interface of one embodiment of an application for the caregiver.

The activities performed by the caregiver mobile device 521 may comprise the auto threshold generation module 519 that would execute control processes on the data collected from the patient wearable device such as the location module 409, and patient inputs such as the threshold values for the sensors, and in conjunction with the data from the activity sensor 408. These threshold values may be used as the initial or default values by the configure sensor thresholds module 515. FIG. 9 shows a screenshot of one example embodiment of the caregiver mobile device that provides the ability for the caregiver to set the threshold values for the sensors 634-645 and the therapy and alert response 647.

The microprocessor 410 can periodically create a time stamped version of the sensor data, by integrating the data from the sensors that detect the environmental stress trigger conditions 402 and physiological stress response symptoms 403 with the timing information from the real time clock module 407. Microprocessor 410 can save the time stamped data from the sensors 102, 103 into the electronic storage module 406. Devices such as a nonvolatile memory card and other data storage media consistent with the spirit of the various embodiments can be used to store the data as presented by storage module 406.

The information stored in the storage module 406, could be retrieved by the caregiver using the retrieve time stamped sensors data module 518 located on the caregiver mobile device 521, through the mobile device communication interface 520, wearable device communication interface 411, and microprocessor 410.

A casual assessment of the relation between antecedent triggers of the stress and the resulting behavior can be mapped by analyzing the chronological data from the sensors. This analysis may aid with the efforts to diagnose the symptoms of conditions such as Autism Spectrum Disorder (ASD) and epilepsy, to understand the factors contributing to the stress, and fine tune the appropriate thresholds of the sensor parameters and therapeutic calming response unique to each patient. Thus, iteratively, the accuracy and reliability of this system at identifying early signs of potential excessive stress conditions such as autistic meltdowns and seizures may be improved.

FIG. 9 is an example embodiment of the patient interface application 630 that can run on the mobile device of the caregiver such as a mobile phone, or any device that supports wireless or internet access to the caregiver. The patient interface includes the display of the status information of the integrated system 631 indicating the components that are active and inactive 633, the status information of the different sensors 102, 103 and their relation to the threshold values 515, the time stamp information such as from a real time clock module 407 of the various events such as the turning on and off of the various components, the exceeding of the sensor values of the corresponding thresholds, the deployment of various therapeutic responses 647. In this example, the patient interface includes an option to control the threshold configuration values 634-645 to meet the specific needs of the patient.

In the FIG. 9, Heat 636, Light 637, Sound 638 and Humidity 639 of the patient's ambient environment are monitored and if they exceed the values respectively 2, 5, 4, 9 then the system would register corresponding "threshold exceeded" event. FIG. 9 example also illustrates a configuration where Heart Rate 642, Breathing Rate 643, Clenching Fists (Muscle tension) 644 and Restlessness 645 of the patient's physiological parameters are monitored and if they exceed the values respectively 7, 8, 6, 9 then the system would register corresponding threshold exceeded event. FIG. 9 shows only a representative list of the ambient environment and physiological parameters and not a comprehensive list of possible parameters.

FIG. 9 also shows the ability to control the caregiver alert and response configuration 646 such as the haptic cue response to the patient, compression vest therapy response to the patient, caregiver alert message response, and music therapy response. In this specific example illustration 647, except the Music Therapy response that is inactivated, the other three responses are set to active mode. The active responses will be delivered when sensor/transducer values exceed their respective thresholds.

Figure 10:
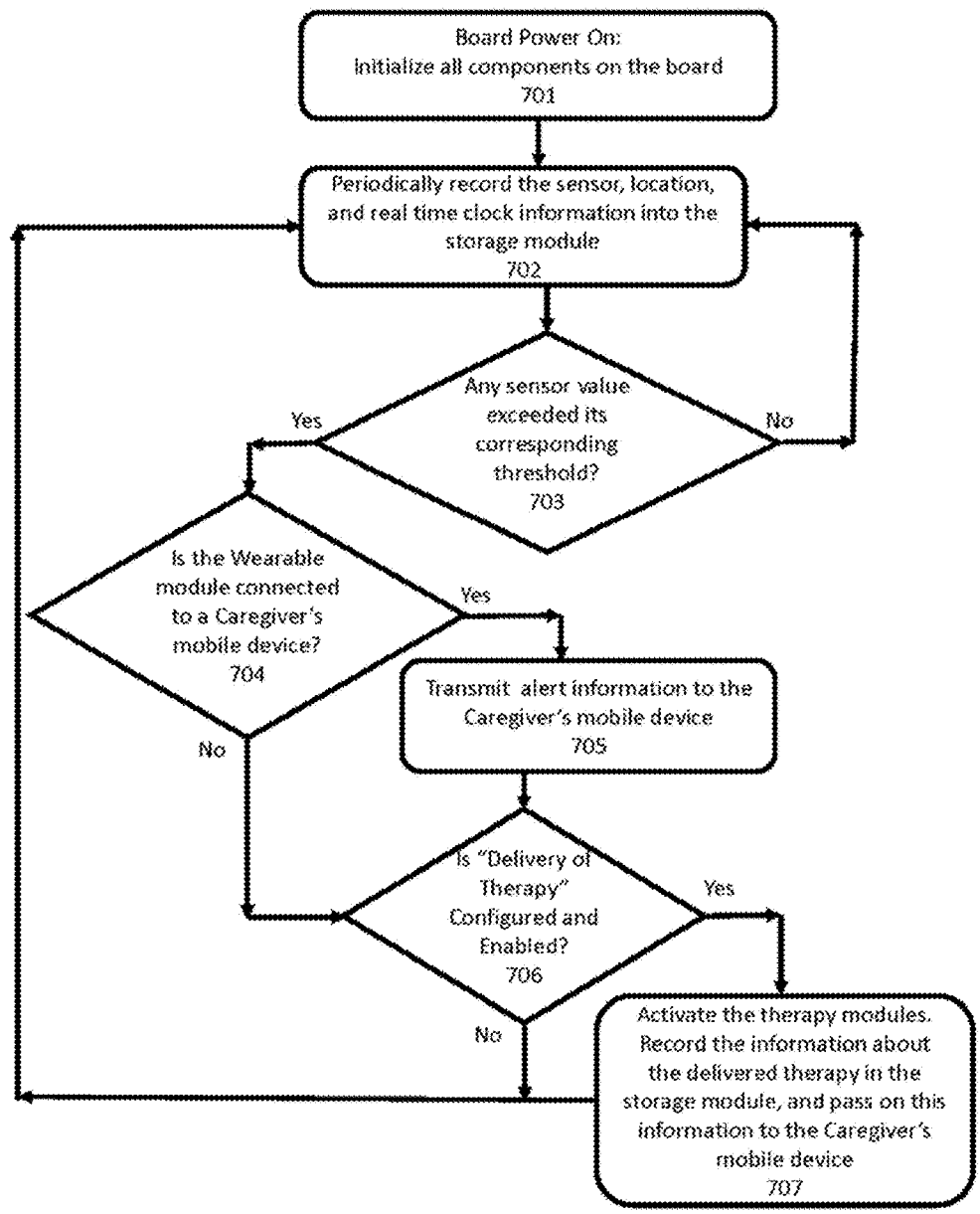
FIG. 10 is a flowchart illustrating one embodiment of the functionality of the device that is wearable by the patient.

FIG. 10 is an example illustration of the control and data flowchart of an embodiment of the wearable device worn by the patient. As noted in the step 701, the wearable device 101 first initializes all the components of the system. After the first iteration 702 of polling and recording the sensor, location and real time clock information into the storage module, the process is repeated periodically until any sensor value exceeds its corresponding threshold 703. If the latter occurs, then the connection between the wearable module and the caregiver's mobile device is evaluated 704. If an active connection exists, then the caregiver's mobile device is alerted 705. Independent of an active connection between the wearable module and the caregiver's mobile device, if the wearable device has been pre-configured to deliver therapy 706, then corresponding therapy is delivered to the patient. This information is communicated to the caregiver's mobile device and also recorded in the storage module 707. This sequence of steps repeat going back to the collection of the sensor, location, and real time clock information 702.

Figure 11:
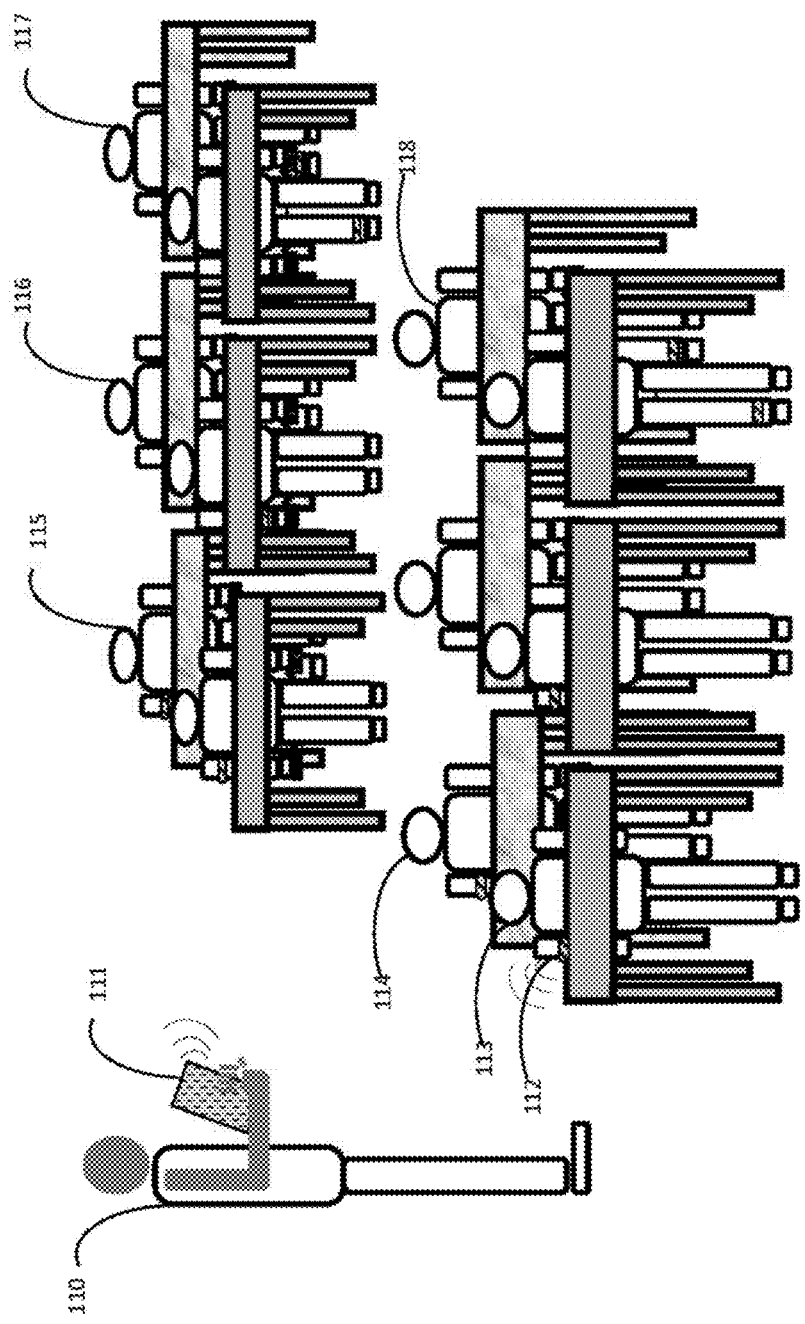
FIG. 11 shows the usage of an example embodiment.

FIG. 11 shows an example usage of an example embodiment. Caregiver 110 is shown using a handheld computer 111 and monitoring the status of several patients' 112-117 emotional and physical response to physiological and environmental conditions.

Figure 12:
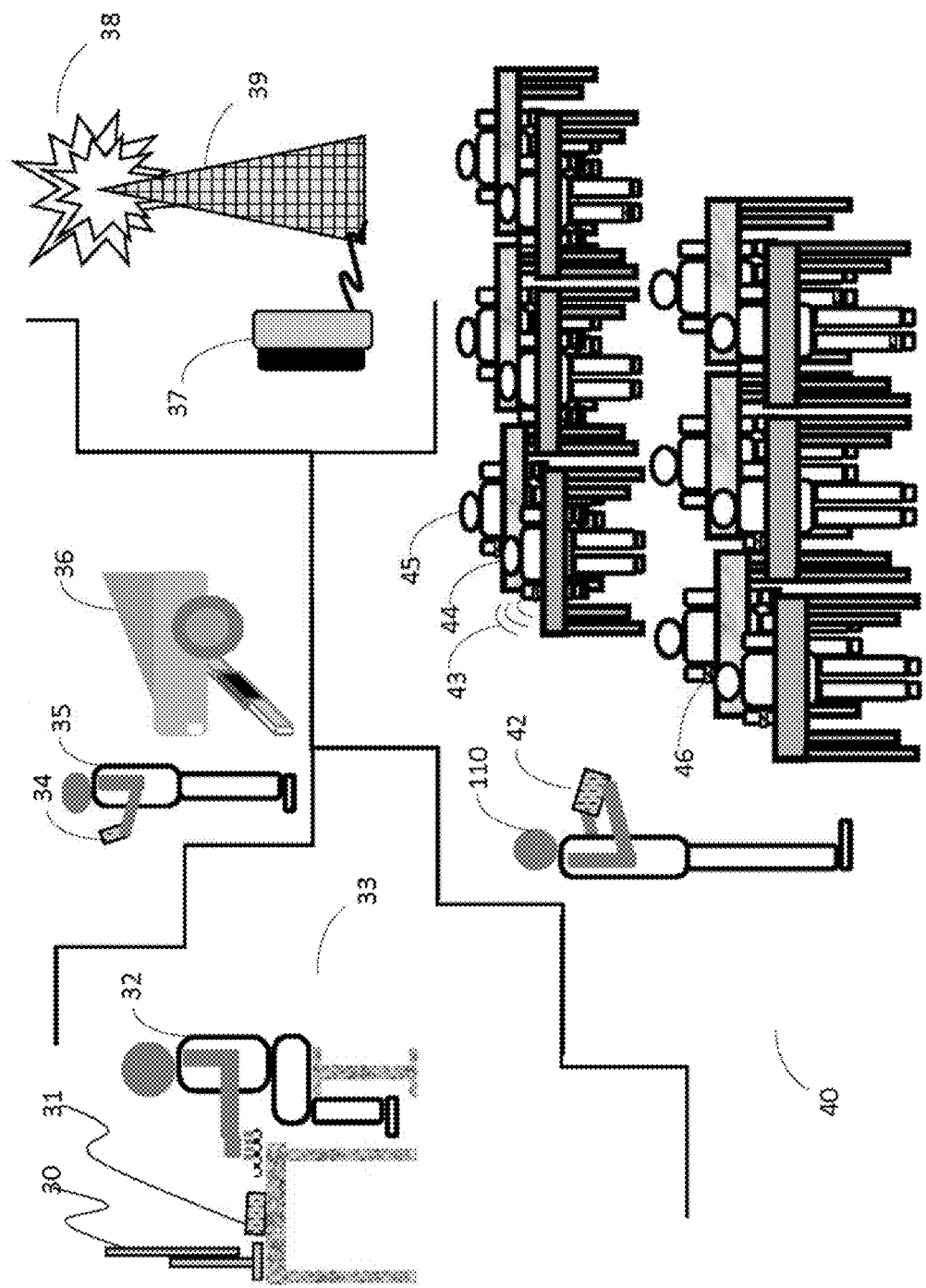
FIG. 12 shows how the status of any one of the patients wearing the device can be reported to either a local caregiver and/or transmitted wirelessly via the internet to a remotely located caregiver.
Figure 13:
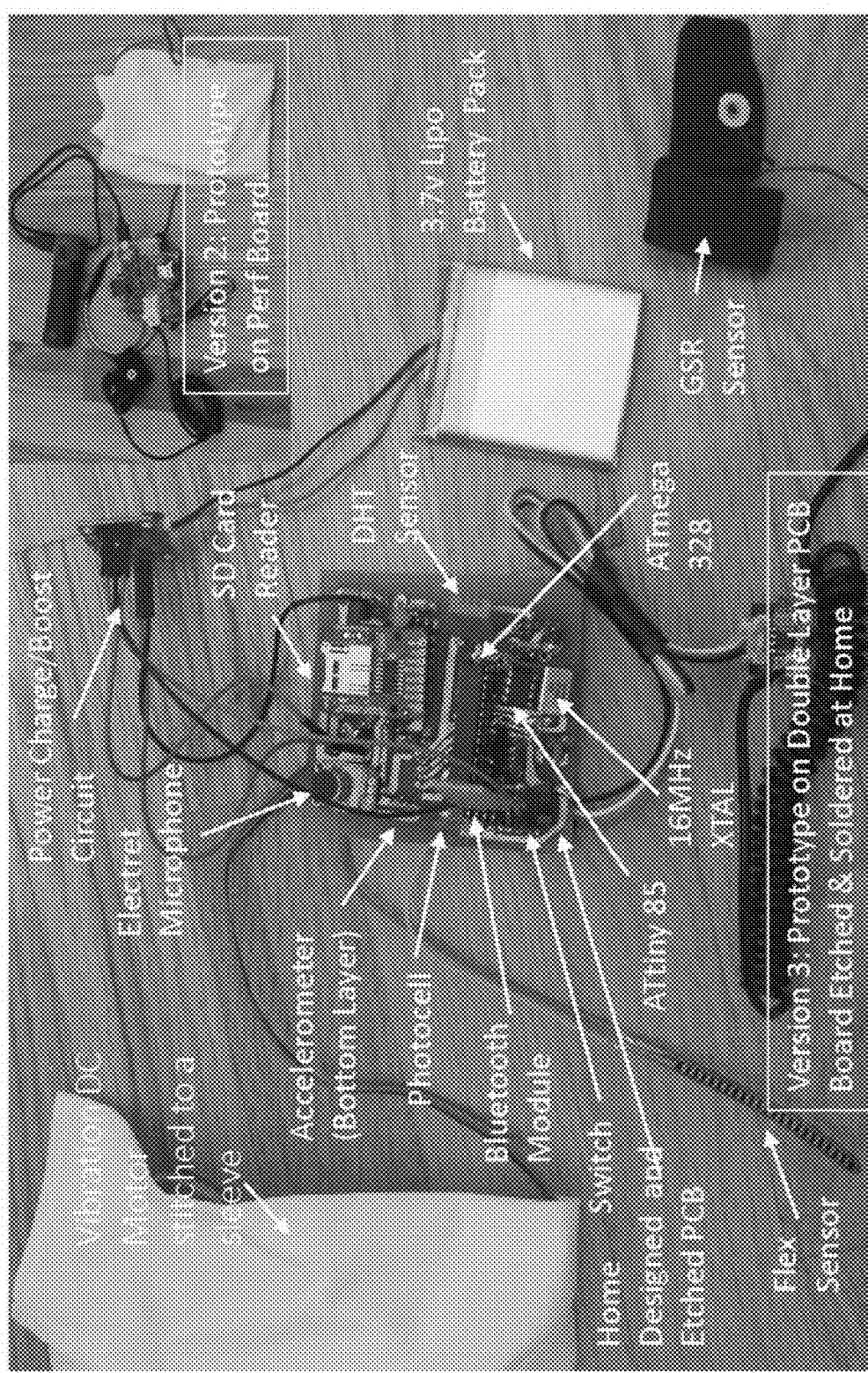
FIG. 13 through FIG. 19 show different example implementations of the wearable device module of an example embodiment that is worn by the patient (not shown).
Figure 14:
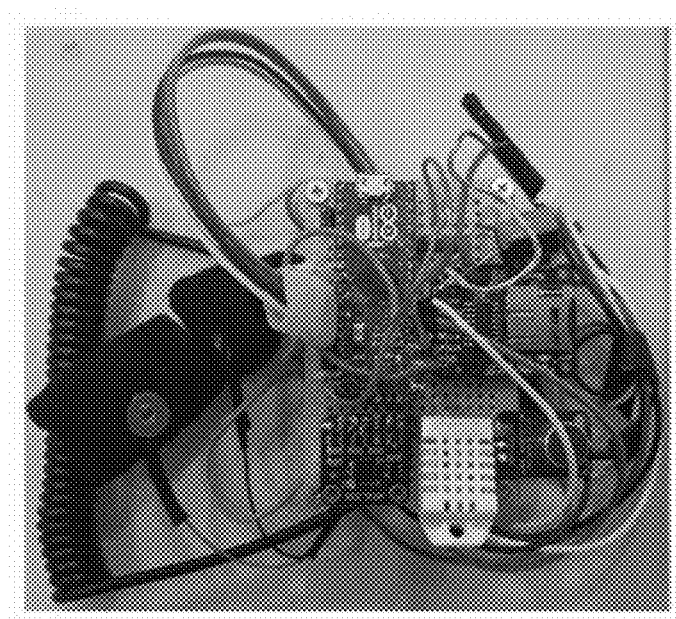
Figure 15:
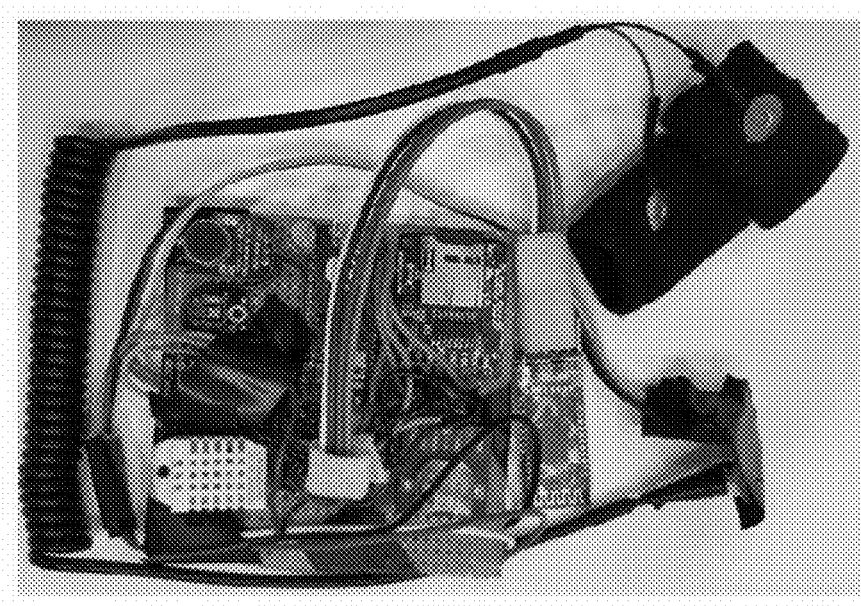
Figure 16:
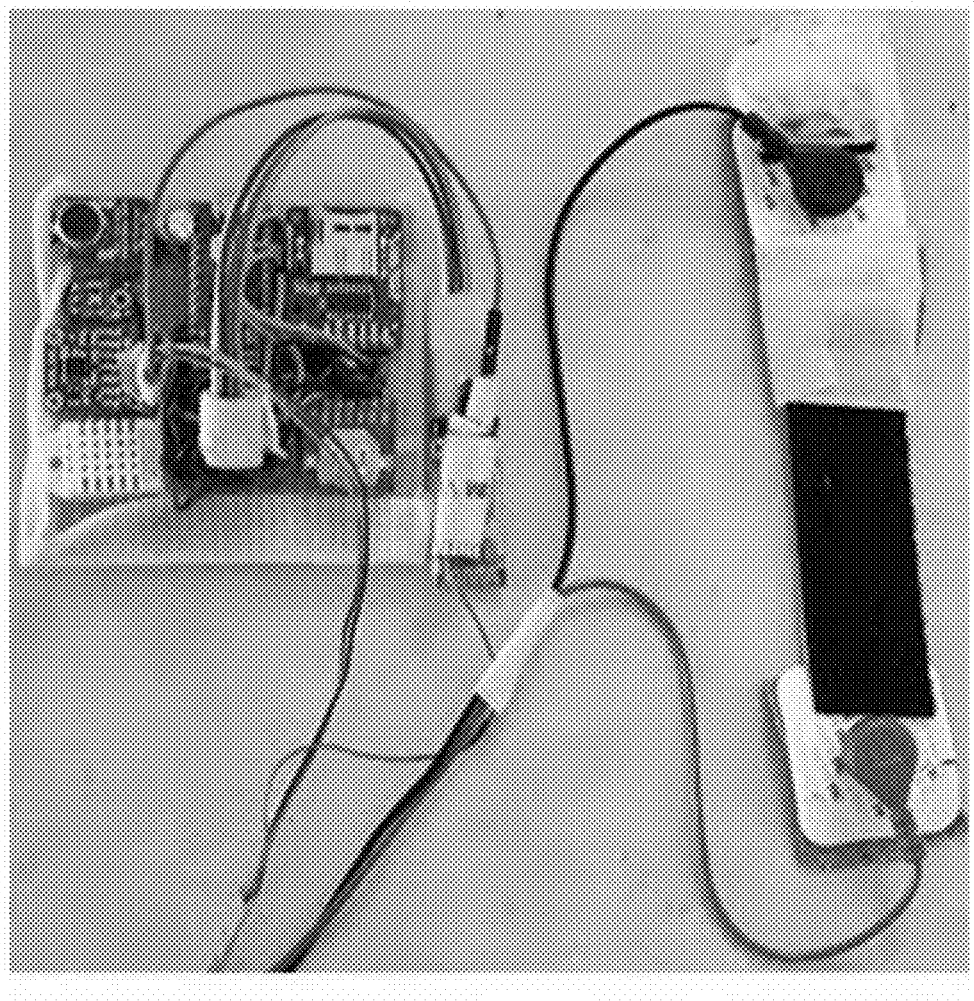
Figure 17:
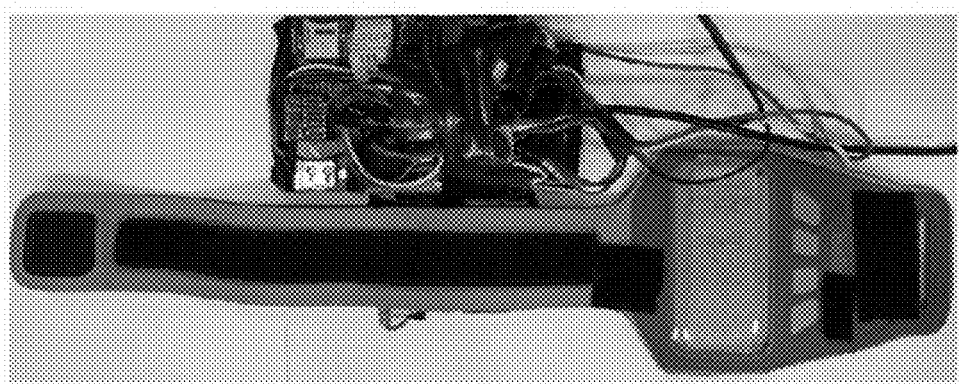
Figure 18:
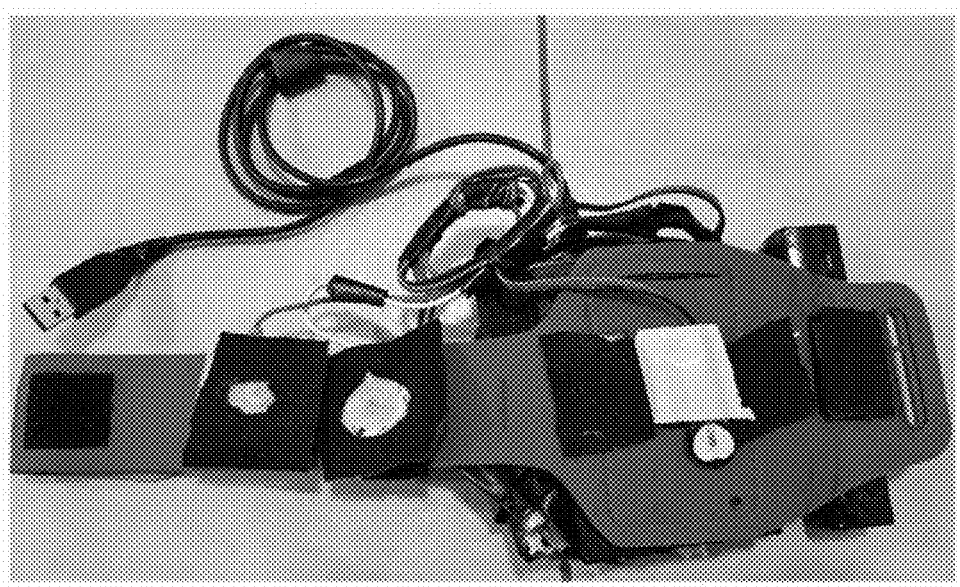
Figure 19:
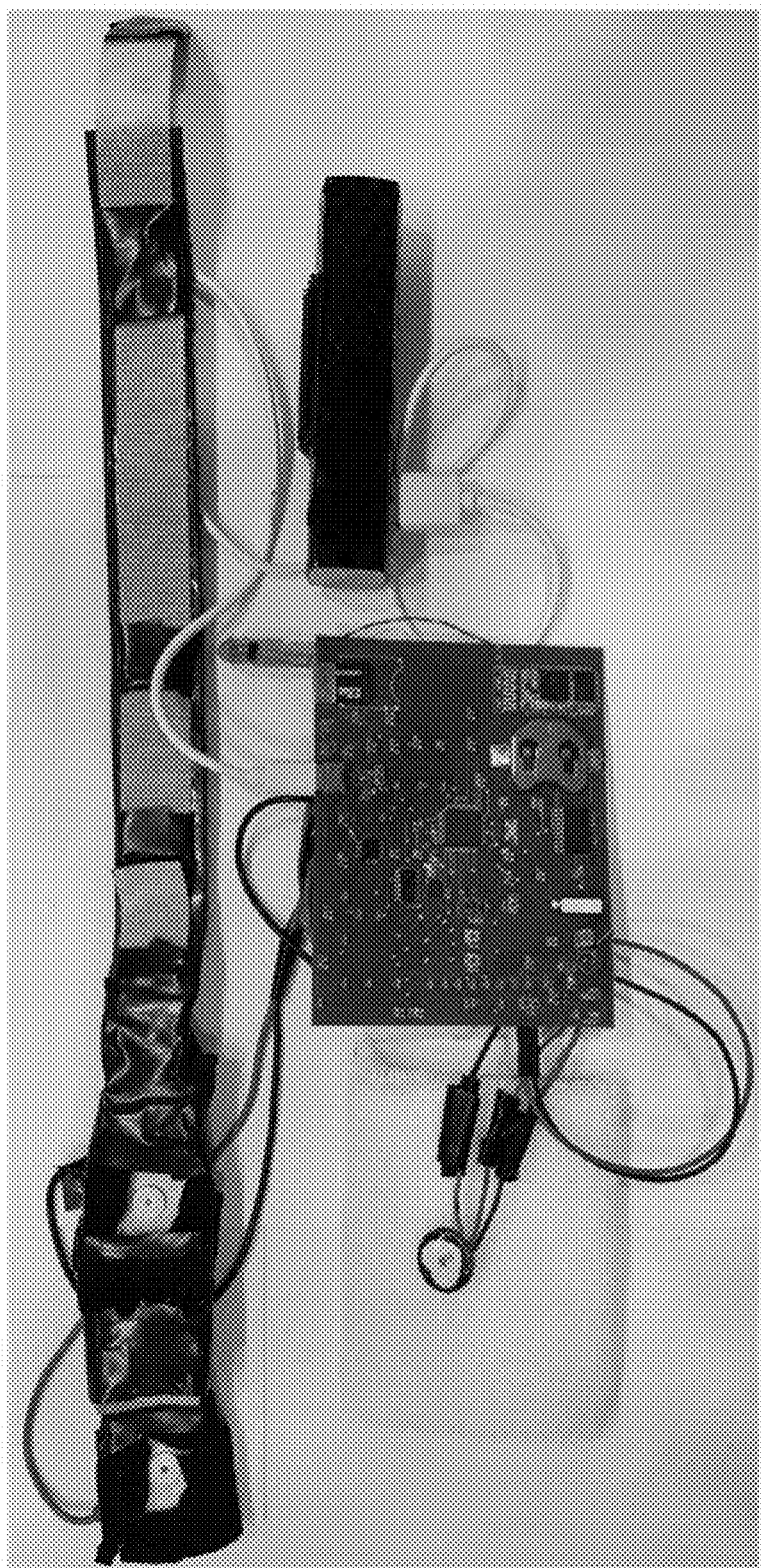
Figure 20B:
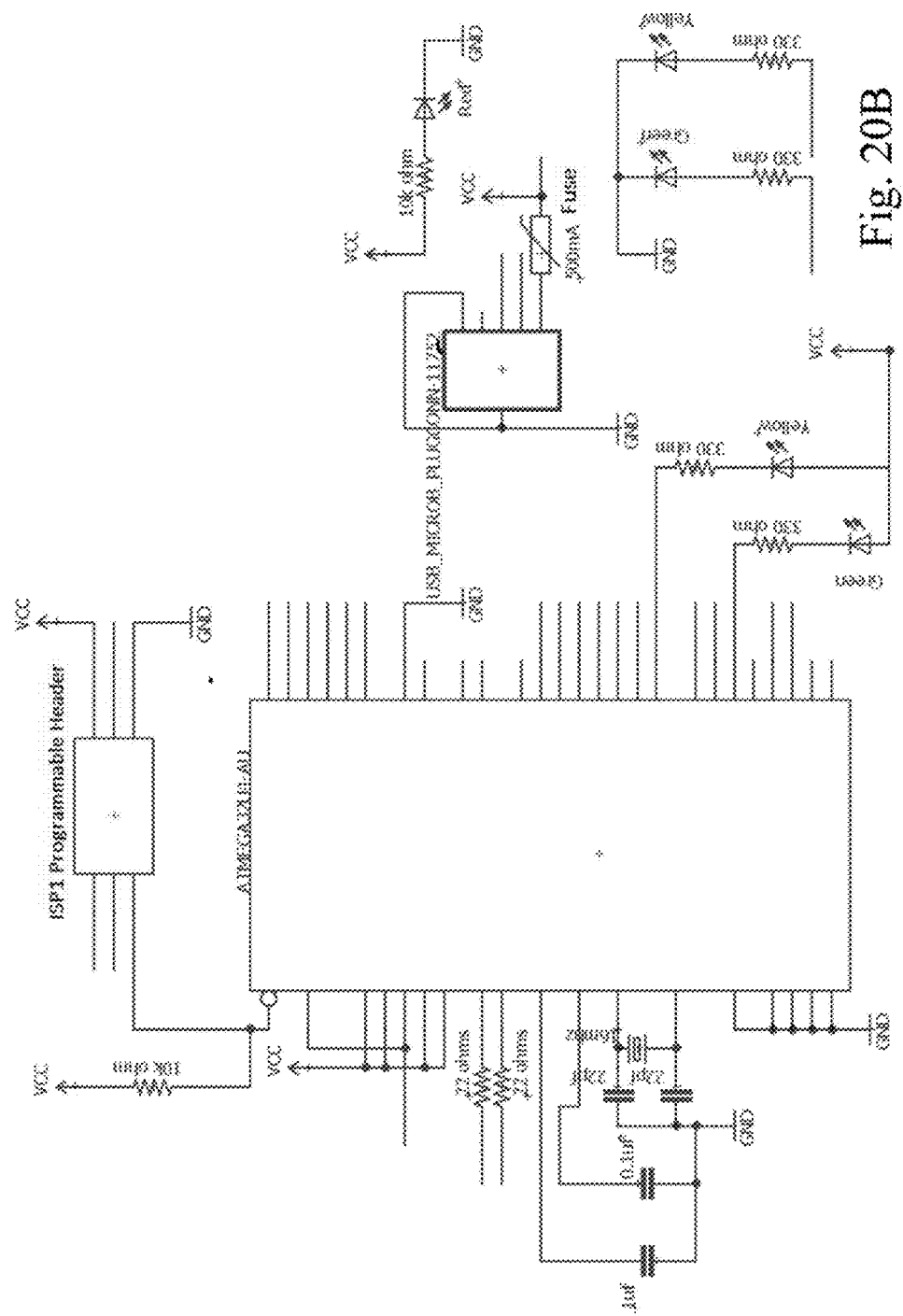
Figure 20C:
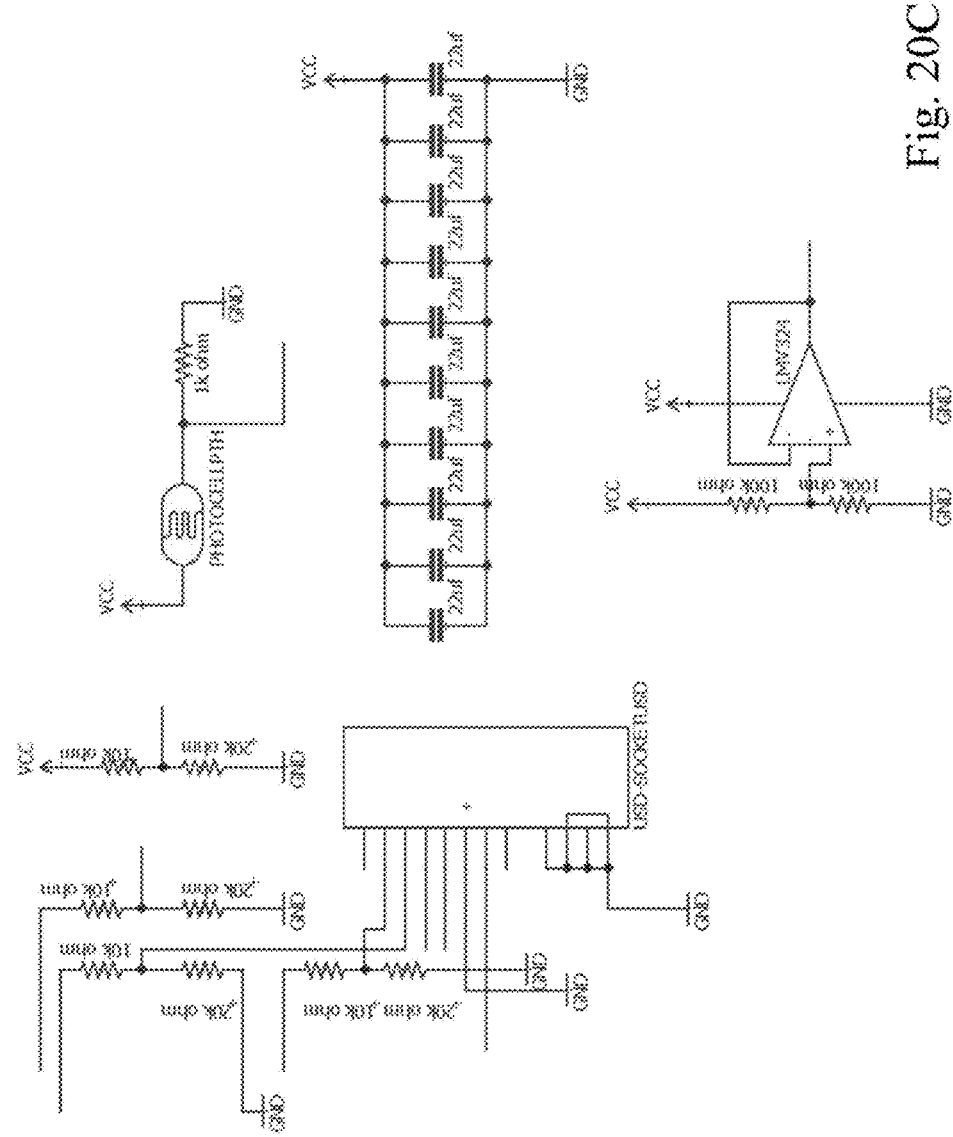
Figure 20D:
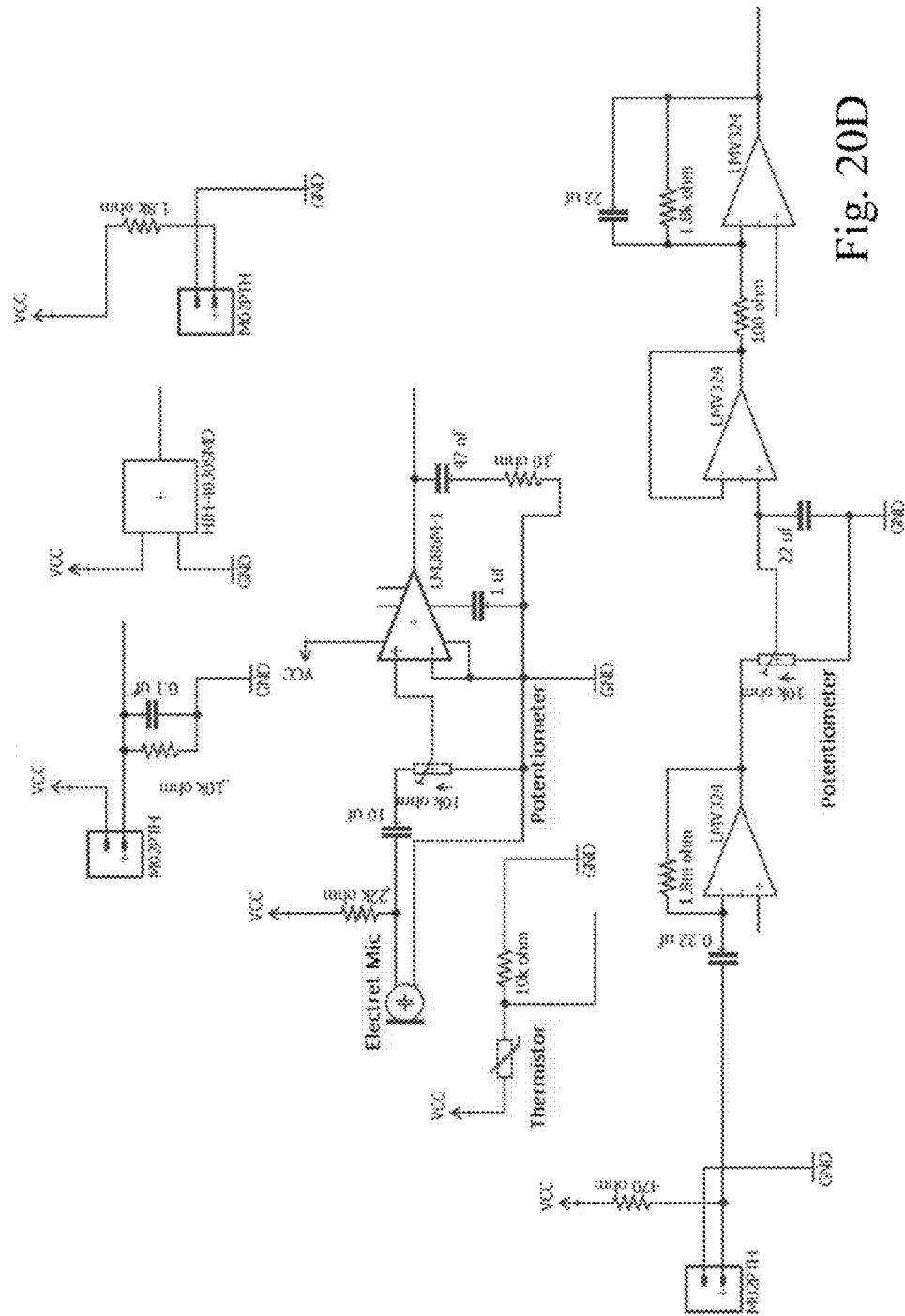
Figure 21:
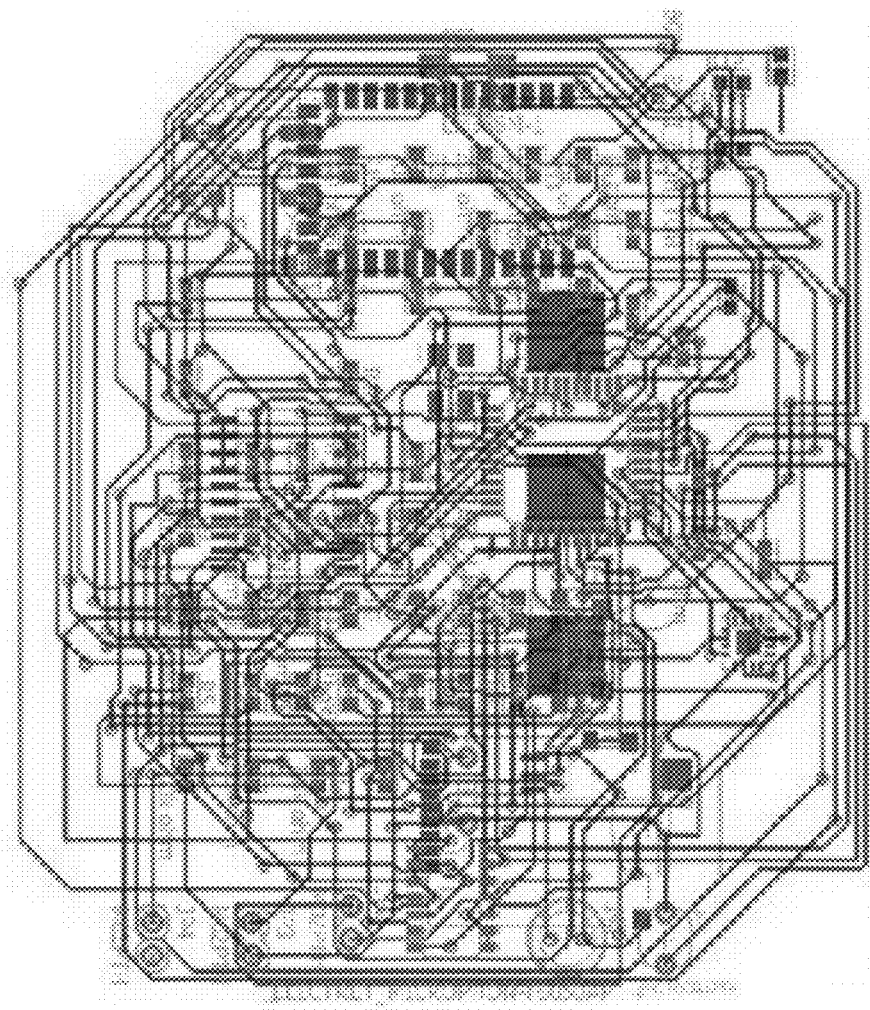

FIG. 12 shows how the status of any one of the patients 112-117 wearing the device can be reported to either a local caregiver 110 and/or transmitted wirelessly 37, 38, 39 via the interne 30, 31 to remotely located caregivers 32, 35.

FIG. 13 through FIG. 19 show different example implementations of the wearable device module 101 that is worn by the patient.

FIGS. 20A through 20D and FIG. 21 show an example electronic circuit layout and electronic circuit schematic implementation of an example embodiment of the wearable device module 101 that is worn by the patient.

Figure 22:
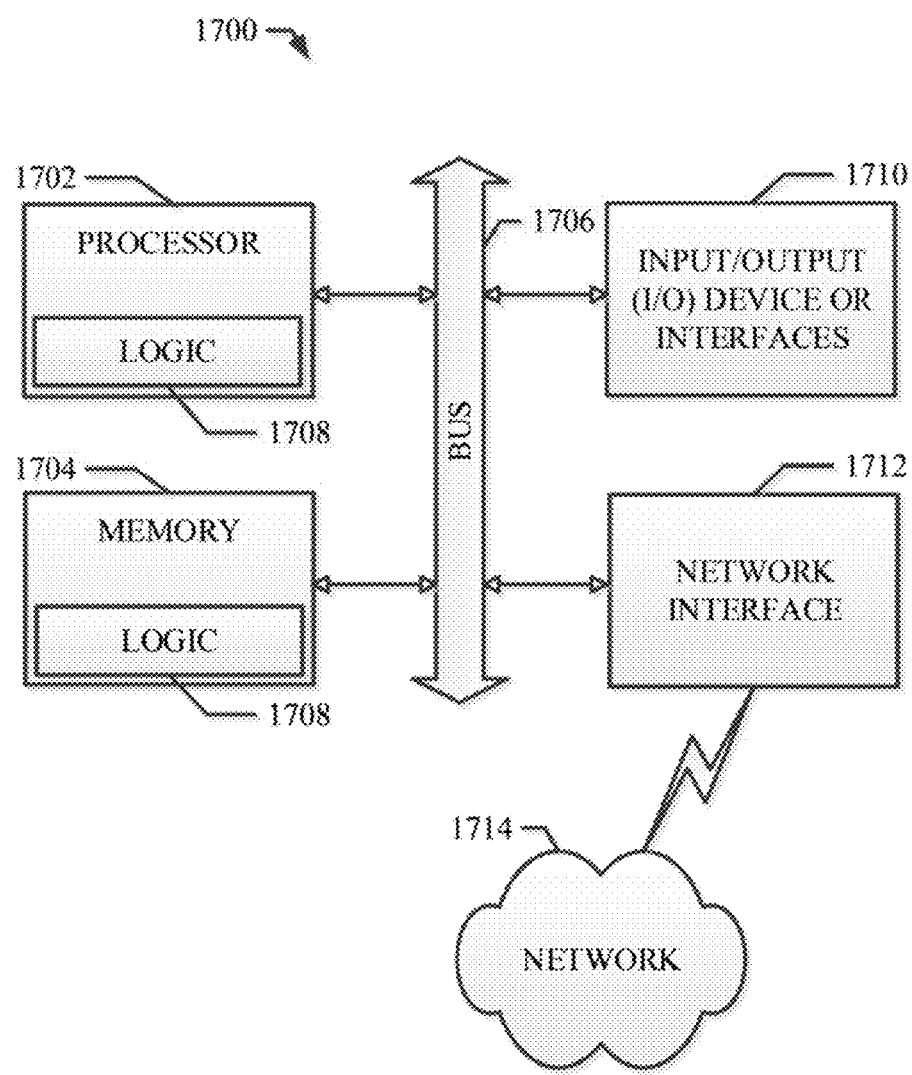
FIG. 22 shows a diagrammatic representation of a machine in the example form of a mobile computing and/or communication system 700 within which a set of instructions when executed and/or processing logic when activated may cause the machine to perform any one or more of the methodologies described and/or claimed herein.

FIG. 22 shows a diagrammatic representation of a machine in the example form of a mobile computing and/or communication system 1700 within which a set of instructions when executed and/or processing logic when activated may cause the machine to perform any one or more of the methodologies described and/or claimed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a laptop computer, a tablet computing system, a Personal Digital Assistant (PDA), a cellular telephone, a smartphone, a web appliance, a set-top box (STB), a network router, switch or bridge, or any machine capable of executing a set of instructions (sequential or otherwise) or activating processing logic that specify actions to be taken by that machine. Further, while only a single machine is illustrated, the term "machine" can also be taken to include any collection of machines that individually or jointly execute a set (or multiple sets) of instructions or processing logic to perform any one or more of the methodologies described and/or claimed herein.

The example mobile computing and/or communication system 1700 includes a data processor 1702 (e.g., a System-on-a-Chip (SoC), general processing core, graphics core, and optionally other processing logic) and a memory 1704, which can communicate with each other via a bus or other data transfer system 1706. The mobile computing and/or communication system 1700 may further include various input/output (I/O) devices and/or interfaces 1710, such as a touchscreen display, an audio jack, and optionally a network interface 1712. In an example embodiment, the network interface 1712 can include one or more radio transceivers configured for compatibility with any one or more standard wireless and/or cellular protocols or access technologies (e.g., 2nd (2G), 2.5, 3rd (3G), 4th (4G) generation, and future generation radio access for cellular systems, Global System for Mobile communication (GSM), General Packet Radio Services (GPRS), Enhanced Data GSM Environment (EDGE), Wideband Code Division Multiple Access (WCDMA), LTE, CDMA2000, WLAN, Wireless Router (WR) mesh, and the like). Network interface 1712 may also be configured for use with various other wired and/or wireless communication protocols, including TCP/IP, UDP, SIP, SMS, RTP, WAP, CDMA, TDMA, UMTS, UWB, WIFI, WIMAX, BLUETOOTH™, IEEE™802.11 x, and the like. In essence, network interface 1712 may include or support virtually any wired and/or wireless communication mechanisms by which information may travel between the mobile computing and/or communication system 1700 and another computing or communication system via network 1714.

The memory 1704 can represent a machine-readable medium on which is stored one or more sets of instructions, software, firmware, or other processing logic (e.g., logic 1708) embodying any one or more of the methodologies or functions described and/or claimed herein. The logic 1708, or a portion thereof, may also reside, completely or at least partially within the processor 1702 during execution thereof by the mobile computing and/or communication system 1700. As such, the memory 1704 and the processor 1702 may also constitute machine-readable media. The logic 1708, or a portion thereof, may also be configured as processing logic or logic, at least a portion of which is partially implemented in hardware. The logic 1708, or a portion thereof, may further be transmitted or received over a network 1714 via the network interface 1712. While the machine-readable medium of an example embodiment can be a single medium, the term "machine-readable medium" should be taken to include a single non-transitory medium or multiple non-transitory media (e.g., a centralized or distributed database, and/or associated caches and computing systems) that stores the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

Depending on the implementation technology and use case, some embodiments may have a subset of these components, or may divide the components into further subcomponents, while some embodiments may merge some of the components.

It is to be understood that the above description is intended to be illustrative, and not restrictive. Many other embodiments will be apparent to those of skill in the art upon reading and understanding the above description. Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

I claim:

1. A method comprising:
   gathering sensor data from a plurality of sensors in a wearable controller configured to be worn by a patient, the sensor data including location and real time clock information, the sensor data further including data corresponding to environmental stimuli around the patient and physiological conditions of the patient;
   determining if a value of the sensor data exceeds corresponding thresholds, the thresholds including environmental thresholds and physiological thresholds;
   determining if an active connection exists between the wearable controller and a caregiver controller;
   sending an alert signal to the caregiver controller, if the active connection exists and only when the value of the sensor data exceeds the corresponding environmental thresholds or physiological thresholds, the caregiver controller configured to wirelessly modify the corresponding environmental thresholds or physiological thresholds of the sensor data on the wearable controller while the sensor data is gathered from the plurality of sensors in the wearable controller;
   determining if the wearable controller is pre-configured to deliver therapy to the patient;
   delivering therapy to the patient via a therapy delivery device in contact with the patient, if the wearable controller is pre-configured to deliver therapy to the patient and only when the value of the sensor data exceeds the corresponding environmental thresholds or physiological thresholds, the therapy delivery device being configured to deliver audible sound or pressure compression to the patient; and
   recording the sensor data, data corresponding to the value of the sensor data that exceeds the corresponding environmental thresholds or physiological thresholds, data corresponding to the alert signal sent to the caregiver controller, and data corresponding to the therapy delivered to the patient.

2. The method of claim 1 wherein the wearable controller is a wearable electro-mechanical controller fastened on a human subject with a harness, the wearable controller including a mobile communication interface and control software to monitor the patient.

3. The method of claim 1 wherein the wearable controller includes a garment with electro-mechanical devices integrated into the garment or a wearable controller configured to temporarily attach and detach from the garment.

4. The method of claim 1 wherein the plurality of sensors includes at least one sensor configured to detect environmental sources of stress, at least one sensor configured to detect physiological stress symptoms, at least one sensor configured to detect the location of the patient, and at least one sensor configured to detect an activity level of the patient.

5. The method of claim 1 wherein the wearable controller includes: a microprocessor, an electronic storage module, a real time clock module, a communication interface, and control software executed by the microprocessor.

6. The method of claim 1 wherein the therapy delivery device is configured to deliver calming therapeutic stress de-escalation stimuli.

7. The method of claim 1 wherein the plurality of sensors includes: at least one sensor configured to detect a light intensity, at least one sensor configured to detect light wavelength, at least one sensor configured to detect sound amplitude, at least one sensor configured to detect sound frequency, at least one sensor configured to detect sound patterns, at least one sensor configured to detect air quality, at least one sensor configured to detect humidity, at least one sensor configured to detect temperature, at least one sensor configured to detect barometric pressure, at least one sensor configured to detect electromagnetic radiation, at least one sensor configured to detect odor of the ambient air, and at least one sensor configured to detect radiofrequency radiation.

8. The method of claim 1 wherein the plurality of sensors includes: at least one sensor configured to detect restlessness of the patient, at least one sensor configured to detect perspiration levels of the patient, at least one sensor configured to detect muscle tension levels of the patient, at least one sensor configured to detect breathing patterns of the patient, and at least one sensor configured to detect audible vocal sound patterns of the patient.

9. The method of claim 1 wherein delivering therapy to the patient via the therapy delivery device includes: playing soothing audio sound that may calm the patient, providing lateral compression massage therapy that may calm the patient, providing dynamic control of a compression vest that may calm the patient, and providing therapeutic pressure on the body of the patient that may calm the patient.

10. The method of claim 1 wherein the caregiver controller includes: control software executed by the caregiver controller and a mobile communication interface to communicate with control software executing on the wearable controller worn by the patient, the control software executed by the caregiver controller being configured to perform the steps of controlling a polling interval of the plurality of sensors, configuring environmental threshold or physiological threshold values of the sensor data, configuring parameters of alert response generation on the caregiver controller, configuring the alert signal on the caregiver controller, configuring the therapy delivered to the patient, retrieving time stamped sensor data from the wearable controller, retrieving the location of the wearable controller, retrieving activity level information of the patient from the wearable controller, and computing a threshold value of the sensor data.

* * * * *